(12) United States Patent
Sosa-Baldivia et al.

(10) Patent No.: US 10,357,006 B2
(45) Date of Patent: Jul. 23, 2019

(54) CHIA VARIETY DESIGNATED REHNBORG

(71) Applicant: ACCESS BUSINESS GROUP INTERNATIONAL LLC, Ada, MI (US)

(72) Inventors: Anacleto Sosa-Baldivia, Zapotiltic (MX); Gerardo Victor Gordillo-Sobrino, Comala (MX)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 16/218,798

(22) Filed: Dec. 13, 2018

(65) Prior Publication Data

US 2019/0183084 A1 Jun. 20, 2019

Related U.S. Application Data

(60) Provisional application No. 62/642,662, filed on Mar. 14, 2018, provisional application No. 62/607,026, filed on Dec. 18, 2017.

(51) Int. Cl.
*A01H 6/50* (2018.01)
*A01H 5/10* (2018.01)

(52) U.S. Cl.
CPC ............ *A01H 6/508* (2018.05); *A01H 5/10* (2013.01)

(58) Field of Classification Search
CPC .................................................. A01H 6/508
See application file for complete search history.

(56) References Cited

U.S. PATENT DOCUMENTS

| 5,445,822 | A | * | 8/1995 | Bracco | ............... | A61K 8/375 |
| | | | | | | 424/401 |
| 5,518,753 | A | * | 5/1996 | Bracco | ............... | A23D 9/00 |
| | | | | | | 426/601 |
| 8,586,831 | B2 | | 11/2013 | Hildebrand | | |
| 8,846,117 | B2 | | 9/2014 | Qu | | |
| 9,686,926 | B2 | | 6/2017 | Sorondo | | |
| 2004/0185129 | A1 | | 9/2004 | Vuksan | | |
| 2013/0136708 | A1 | | 5/2013 | Qu et al. | | |
| 2014/0325694 | A1 | | 10/2014 | Sorondo | | |

OTHER PUBLICATIONS

Jamboonsri et al, 2010 Genet. Resour. Crop Evol. 59: 171-178.*
International Search Report and Written Opinion dated Feb. 15, 2019 for Application No. PCT/US2018/065364.
Sosa, et al., "Chia crop (*Salvia hispanica* L): its history and importance as a source of polyunsaturated fatty acids omega-3 around the world: a review," J. Crop Res. Fert. 1(104): 1-9 (2016).
Sosa et al., "Agronomic and physiological parameters related to seed yield of white chia (*Salvia hispanica* L)," Acta Fitogenética 3:31 (2016).
Sosa et al., "Plant traits related to seed yield and their heritability on white chia (*Salvia hispanica* L.)," Acta Fitogenetica 3:32 (2016).
Baginsky et al. "Growth and yield of chia (*Salvia hispanica* L.) in the Mediterranean and desert climates of Chile," Chilean J. Agric. Res. 76(3): 255-264 (2016).
Cahill, "Human selection and domestication of chia (*Salvia hispanica* L.)," J. Ethnobiol. 25:155-174 (2005).
Cahill, "Ethnobotany of Chia *Salvia hispanica* L. (Lamiaceae)," Econ. Bot. 57: 604-618 (2003).
Ali et al., "The Promising Future of Chia, *Salvia hispanica* L.," J. Biomedicine Biotech. vol. 2012, Article ID 171956, 1-9 (2012).
Souza et al. "Initial growth of chia (*Salvia hispanica* L) submitted to nitrogen, phosphorus and potassium fertilization," Australian J. Crop Sci. (AJCS) 11(05):610-615 doi: 10.21475/ajcs.17.11.05. (2017).
Jamboonsri et al., "Extending the range of an ancient crop, *Salvia hispanica* L.—a new omega-3 source," Genet. Resour. Crop Evol. 59:171-178 (2012).

* cited by examiner

*Primary Examiner* — David H Kruse
(74) *Attorney, Agent, or Firm* — Brinks Gilson & Lione

(57) ABSTRACT

Described herein is a chia (*Salvia hispanica* L.) variety designated Rehnborg, seed thereof, hybrids thereof, products thereof, and cultivars derived therefrom. The Rehnborg variety has uniform white seed, greater seed mass, and greater seed yields compared to other typical chia varieties or wild-type chia.

27 Claims, 10 Drawing Sheets

A　　　　　　　B　　　　　　　C

D　　　　　　　E　　　　　　　F

A      B      C      D

A    B    C    D

A    B    C    D

A   B   C   D

A    B    C    D ically colder and hard freezes occur. See, Sosa et al., "Chia
CHIA VARIETY DESIGNATED REHNBORG

CROSS REFERENCE TO RELATED APPLICATIONS

This application claims priority to U.S. Provisional Patent Application No. 62/607,026, filed on Dec. 18, 2017 and U.S. Provisional Patent Application No. 62/642,662, filed on Mar. 14, 2018, each of which is incorporated herein in its entirety by express reference thereto.

TECHNICAL FIELD

Described herein is a new chia (*Salvia hispanica* L.) variety designated Rehnborg, seeds thereof, hybrids thereof, products thereof, and cultivars derived therefrom.

BACKGROUND

Chia (*Salvia hispanica* L.) is a member of the Lamiaceae or mint family. The chia plant is a dicotyledonous annual that reaches about 1.75 m in height. The plants have opposed leaves that are 4-8 cm long and 3-5 cm wide. The flowers are purple, blue, or white and the inflorescence is a pedicellate having six or more flowers on the rachis. Chia seeds are small ovals with a diameter of about 1 mm. The seed color can be black, brown, mottled, or white. Chia is grown commercially for its seeds that are rich in omega-3 polyunsaturated fatty acids (58-64% of total lipids; 31-35% lipids by mass of the seed). Chia and chia oil are used as human and animal food and the oil is used in cosmetics and paints. The chia seed is also rich in protein (16-24% by mass of seed) and fiber (34-56% by mass of seed). Sosa, et al., "Chia crop (*Salvia hispanica* L.): its history and importance as a source of polyunsaturated fatty acids omega-3 around the world: a review," *J. Crop Res. Fert.* 1(104): 1-9 (2016).

Chia was domesticated in Mesoamerica around 2600 B.C. and was a staple food in Mexico between 1500 and 900 B.C. See Baginsky et al. "Growth and yield of chia (*Salvia hispanica* L.) in the Mediterranean and desert climates of Chile," *Chilean J. Agric. Res.* 76(3): 255-264 (2016). Chia is typically grown in tropical and subtropical areas in latitudes ranging from north 20° 55' north to 25° 05' south and altitudes from 400 m to 2500 m above mean sea level, such as Australia, Bolivia, Colombia, Guatemala, Mexico, Peru, and Argentina. The plants are sensitive to frost at all development stages and generally cannot be cultivated at higher latitudes and altitudes.

Mexico produces the majority of commercial chia and the Pinta variety is the most commonly cultivated chia variety. Cahill, "Human selection and domestication of chia (*Salvia hispanica* L.)," *J. Ethnobiol.* 25:155-174 (2005). Pinta is native to Jalisco, Mexico and approximately 80% of chia grown in Mexico is the Pinta variety. Cahill, "Ethnobotany of Chia *Salvia hispanica* L. (Lamiaceae)," *Econ. Bot.* 57: 604-618 (2003). Pinta produces a combination of black and white seeds at a ratio of 9 black to 1 white. See Rovati et al., "Particularidades de la semilla de chia (*Salvia hispánica* L.)," *EEAOC—Avance Agroindustrial.* 33: 39-43 (2012). The Chiablanca SC DE RL Company, Jalisco, Mexico, developed a variety known as White Acatic that produces a ratio of white to black seeds of 24:1 (~96% white seeds).

The Sahi Alba 914 variety was developed in Argentina by TFSB LLC, located in Dover Del., USA. See U.S. Pat. No. 9,686,926, which is incorporated by reference herein. The Heartland variety was developed by the University of Kentucky, Lexington, Ky., USA. See U.S. Pat. No. 8,586,831, which is incorporated by reference herein. There are two presentations of Heartland, one with white seeds and the other with black seeds. Both Sahi Alba 914 and one presentation of Heartland have uniform white seeds. These varieties were developed to bloom in latitudes above 23° north or below 23° south where the photoperiod is greater than 12.5 hours. The Sahi Alba 914 and Heartland varieties are capable of producing chia seed in agricultural zones of the United States and Argentina where the weather is typically colder and hard freezes occur. See, Sosa et al., "Chia crop (*Salvia hispanica* L.): its history and importance as a source of polyunsaturated fatty acids omega-3 around the world: a review," *J. Crop Res. Fert.* 1(104): 1-9 (2016).

Both the seed color and seed mass are important for commercial chia production. The color and mixtures of multiple seed colors (e.g., black, brown, mottled, or white) affects the final color of the product and can lead to color inconsistency among harvests. This is particularly important when the seed oil is used for cosmetics. Uniform seed color is desirable and white seeds are preferable because the oil has a lighter color. In addition, a high seed mass is preferable for a commercial crop because each seed produces more product. The current commercial varieties of chia have variable seed masses ranging from about 840 to about 1325 mg per 1000 seeds. See Table 1, infra. This variability affects the harvest yields of the seed product. Lower seed masses produce a lower yield of seed per hectare.

Previous breeding efforts have predominately focused on developing domesticated chia varieties or those that can be cultivated in temperate regions. Few efforts have been made to generate chia varieties that have uniform seed color and enhanced seed yields. Therefore, there is a need to develop new chia (*Salvia hispanica* L.) varieties that have uniform seed color, greater seed mass, and high seed yields.

SUMMARY

Described herein is a chia (*Salvia hispanica* L.) variety designated Rehnborg, seeds thereof, hybrids thereof, products thereof, and cultivars derived therefrom. The Rehnborg variety has uniform white seed, greater seed yields, and greater seed mass compared to other chia varieties and wild type chia plants.

One embodiment described herein is a seed of chia (*Salvia hispanica* L.) variety designated Rehnborg, a representative sample of seed having been deposited under ATCC Patent Deposit Designation PTA-124758. In one aspect, at least about 99% of the seed has a white seed color. In another aspect, the seed has an average seed mass of at least about 1400 mg/1000 seeds.

Another embodiment described herein is a plant product produced from one or more of the Rehnborg variety seeds. In one aspect, the product comprises chia seed, oil, meal, protein, fiber, derivatives thereof, or combinations thereof. Another aspect is chia oil or meal produced from one or more of the Rehnborg variety seeds. Another aspect is a cosmetic or beauty product comprising chia oil produced from one or more of the Rehnborg variety seeds. Another aspect is a food product comprising one or more of the Rehnborg variety seeds.

Another embodiment described herein is a chia plant, or part thereof, produced by growing a seed of chia (*Salvia hispanica* L.) variety designated Rehnborg, a representative sample of seed having been deposited under ATCC Patent Deposit Designation PTA-124758. In one aspect, the plant is produced without genetic engineering or mutagenesis. Another aspect is a homogenous population comprising two or more chia plants produced by growing Rehnborg variety seeds. In another aspect, the homogenous population comprising two or more chia plants produced by growing Rehnborg variety seed yields an average of at least about 1500 kilograms of seed per hectare. In another aspect, the Rehnborg chia plant comprises or confers to its seed one or more traits comprising increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants or wild type chia.

Another embodiment described herein is a tissue culture of cells produced from the Rehnborg chia plant, wherein the cells are produced from a plant part comprising embryo, meristematic cell, leaf, cotyledon, hypocotyl, root, root tip, stem, pistil, anther, ovule, flower, pollen, or seed. Another aspect is a chia (*Salvia hispanica* L.) plant regenerated from tissue culture, wherein the chia plant comprises the morphological and physiological characteristics of variety Rehnborg, a representative sample of seed having been deposited under ATCC Patent Deposit Designation PTA-124758.

Another embodiment described herein is a chia (*Salvia hispanica* L.) plant or plant part of the variety designated Rehnborg, a representative sample of seed having been deposited under ATCC Patent Deposit Designation PTA-124758. One aspect is a homogenous population of two or more Rehnborg chia plants, wherein the population yields an average of at least about 1500 kilograms of seed per hectare. Another aspect is chia seed produced from the Rehnborg chia plants. In another aspect, at least about 99% of the Rehnborg seed has a white seed color. In another aspect, the Rehnborg chia seed has an average seed mass of at least about 1400 mg/1000 seeds. In another aspect, the Rehnborg chia plant or plant part comprises one or more traits comprising increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants or wild-type chia.

Another embodiment described herein is a descendant of a Rehnborg chia plant, wherein the descendant comprises one or more traits comprising increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants or wild-type chia.

Another embodiment described herein is a germplasm of chia (*Salvia hispanica* L.) variety designated Rehnborg, a representative sample of seed having been deposited under ATCC Patent Deposit Designation PTA-124758. One aspect is a chia plant comprising the Rehnborg chia variety germplasm. Another aspect is chia seed produced by a chia plant comprising the Rehnborg chia variety germplasm. In another aspect, at least about 99% of the chia seed has a white seed color. In another aspect, the chia seed has an average seed mass greater than about 1400 mg/1000 seeds. Another aspect is a homogenous population of chia plants comprising the Rehnborg chia variety germplasm, wherein the population yields an average of at least about 1500 kilograms of seed per hectare. Another aspect is a descendant plant comprising the Rehnborg chia variety germplasm. Another aspect is a plant product comprising the Rehnborg chia variety germplasm.

Another embodiment described herein is a method for producing a chia seed, the method comprising: (a) planting a seed of chia (*Salvia hispanica* L.) variety designated Rehnborg, a representative sample of seed having been deposited under ATCC Patent Deposit Designation PTA-124758 in pollinating proximity to itself or to a seed from a different chia variety; (b) growing a plant from the seeds planted in pollinating proximity; and (c) harvesting one or more resultant chia seeds. In one aspect, the chia seed has average seed mass greater than about 1400 mg/1000 seeds or an average seed yield of at least about 1500 kilograms of seed per hectare. Another aspect is a plant product from chia seed produced by the foregoing method. In one aspect, the plant product is chia seed, oil, or meal. Another aspect is a food or cosmetic product comprising a plant product from chia seed produced by the foregoing method. Another aspect is a descendant plant grown from chia seed produced by the foregoing method.

Another embodiment described herein is a method for producing a chia (*Salvia hispanica* L.) variety Rehnborg seed, the method comprising: (a) crossing a chia plant (*Salvia hispanica* L.) variety designated Rehnborg, a representative sample of seed having been deposited under ATCC Patent Deposit Designation PTA-124758, with a plant of a second, different chia (*Salvia hispanica* L.) variety Rehnborg to produce $F_1$ chia seed; and (b) harvesting the $F_1$ chia seed. Another aspect is an $F_1$ chia (*Salvia hispanica* L.) seed produced by the foregoing method. Another aspect is a plant product from a chia plant or seed produced by the foregoing method. Another aspect is a descendant plant or seed from a chia plant or seed produced by the foregoing method.

Another embodiment described herein is a method of introducing a desired trait into chia (*Salvia hispanica* L.) variety Rehnborg, the method comprising: (a) crossing chia plant (*Salvia hispanica* L.) variety designated Rehnborg, a representative sample of seed having been deposited under ATCC Patent Deposit Designation PTA-124758, with a plant of another chia (*Salvia hispanica* L.) variety that comprises a desired trait to produce $F_1$ progeny plants; (b) selecting one or more progeny plants that have the desired trait to produce selected progeny plants; (c) crossing the selected progeny plants with the Rehnborg plants to produce backcross progeny plants; (d) selecting for backcross progeny plants that have the desired trait; and (e) repeating steps (c) and (d) three or more times in succession to produce fourth or higher backcross progeny plants that comprise the desired trait. Another aspect is a chia (*Salvia hispanica* L.) plant produced by the foregoing method, wherein the plant comprises traits and physiological and morphological characteristics of chia (*Salvia hispanica* L.) variety Rehnborg, a representative sample of seed having been deposited under ATCC Patent Deposit Designation PTA-124758. In one aspect, the desired trait comprises one or more of: increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants. Another aspect is a plant product from a chia plant or seed produced by the foregoing method. Another aspect is a descendant plant or seed from a chia plant or seed produced by the foregoing method.

Another embodiment described herein is a method for selecting a chia (*Salvia hispanica* L.) plant comprising the traits and the physiological and morphological characteristics of chia (*Salvia hispanica* L.) variety Rehnborg, a representative sample of seed having been deposited under ATCC Patent Deposit Designation PTA-124758, the method comprising: performing a plurality of mass selections; and performing a plurality of plant by plant selections, wherein the selection selects for one or more of white seed color, increased seed mass, or enhanced seed yield. One aspect is a chia plant produced by the foregoing method, wherein the plant comprises traits and physiological and morphological characteristics of chia (*Salvia hispanica* L.) variety Rehnborg, a representative sample of seed having been deposited under ATCC Patent Deposit Designation PTA-124758. Another aspect is a chia seed form a plant produced by the foregoing method, wherein the plant comprises traits and physiological and morphological characteristics of chia (*Salvia hispanica* L.) variety Rehnborg, a representative sample of seed having been deposited under ATCC Patent Deposit Designation PTA-124758. Another aspect is germplasm of chia plant or seed produced by the foregoing method wherein the plant or seed comprises traits and physiological and morphological characteristics of chia (*Salvia hispanica* L.) variety Rehnborg. Another aspect is a plant product from a chia plant or seed produced by the foregoing method. Another aspect is a descendant plant or seed from a chia plant or seed produced by the foregoing method.

DETAILED DESCRIPTION

Figure 1:
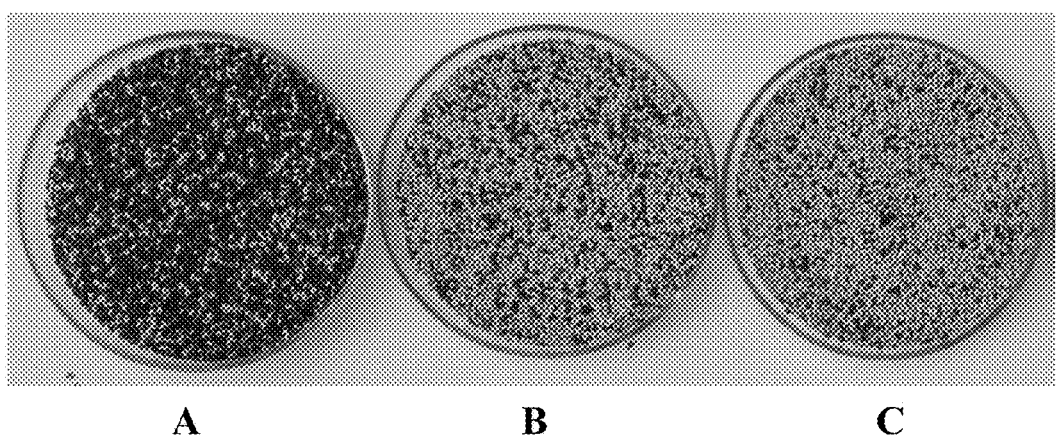
FIG. 1. Seed samples during the selection cycle leading to the Rehnborg variety. Table 2 shows the complete selection cycle. Seed samples: (A) First mass selection (2010), 8% white seed; (B) Second mass selection (2011), 77% white seed; (C) Third mass selection (2012), 90% white seed; (D) First plant by plant selection (2013); 98% white seed; (E) Second plant by plant selection (2014); 99% white seed; (F) Third plant by plant selection (2015), 100% white seed (Rehnborg variety).
Figure 1:
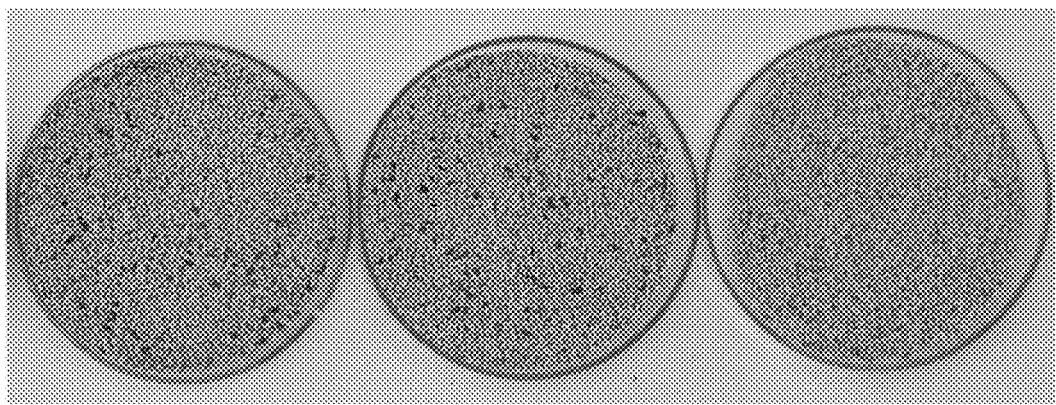

Described herein is a chia (*Salvia hispanica* L.) variety designated Rehnborg that has uniform white seeds, greater seed yields, and greater seed mass compared to other typical chia varieties or wild-type chia.

The phrase "agriculturally advantageous trait" or "agriculturally advantageous characteristic" as used herein refers to one or more traits that confer a growth advantage, production enhancement, or commercial benefit. Such traits or characteristics include, but are not limited to, increased metabolic efficiency; greater photosynthetic capacity; increased or more rapid growth rate; greater seed yield; greater seed weight; modified plant architecture; herbicide resistance; reduced or increased height; reduced or increased branching; reduced or increased number of leaves; increased or decreased number of inflorescence; increased or decreased inflorescence length; total biomass; increased or decreased days to flowering; increased or decreased days to maturity; increased harvest index; enhanced cold or frost tolerance; improved vigor; enhanced color; increased color uniformity; greater product uniformity; enhanced resistance to insects, predators, or disease; improved storage characteristics; enhanced yield; greater water optimization; greater tolerance to dehydration, water deficit conditions, or drought; better recovery from dehydration, water deficit conditions, or drought; increased root growth; increased lateral root formation; increased root branching; increased surface area of roots; increased root mass; more root hairs; increased nutrient or fertilizer uptake; increased micronutrient uptake; enhanced salt tolerance; enhanced resistance of plant tissue to decay; enhanced heavy metal tolerance; enhanced sweetness; improved texture; decreased phosphate content; increased germination; increased oil content; increased protein content; increased carbohydrate content; increased fiber content; improved starch composition; improved flower longevity; enhanced health and nutritional characteristics; production of novel oils or resins; production of novel proteins or peptides; production of novel carbohydrates; enhanced agronomic traits; enhanced heritability of any of the foregoing traits, or any other agronomically desirable or commercially advantageous traits or characteristics.

The term "backcrossing" as used herein refers to a process where a progeny plant is crossed back to one of the parental genotypes one or more times. For example, crossing a first generation hybrid $F_1$ with one of the parental genotypes of the $F_1$ hybrid, and then crossing a second-generation hybrid $F_2$ with the same parental genotype, and so forth. Backcrossing is typically used to introduce one or more locus conversions from one genetic background into another.

The term "breeding" as used herein refers to the genetic manipulation of living organisms.

The term "cell" as used herein refers a plant cell, whether isolated, in tissue culture, or incorporated in a plant or plant part.

The term "cross pollination" refers to fertilization by the union of two gametes from different plants.

The terms "days after sowing" or "DAS" as used herein refers to the number of days following planting that a characteristic is observed, such as flowering or reaching maturity.

The term "descendant" as used herein refers to any generation plant.

The term "derived from" as used herein, unless otherwise specified, indicates that a particular thing (e.g., plant, seed, etc.) or group of things has originated from the source specified, but has not necessarily been obtained directly from the specified source.

The term "$F_n$" as used herein refers to the filial generation, where the subscript n refers to the generation number, such as $F_1$, $F_2$, $F_3$, etc.

The terms "improved," "increased," "enhanced," or "greater" as used herein refer to the heightening or bettering of a particular characteristic or trait as compared to other similar organisms or a wild-type organism. Typically, this is an agriculturally advantageous trait.

The term "plant" as used herein refers to a plant at any developmental stage, as well as any part or parts of a plant that may be attached to or separated from an intact plant.

The term "plant part" as used herein comprises organs, tissues, and cells of a plant. Plant parts comprise leaves, stems, shoots, petioles, roots, root tips, root caps, root hair, leaf hair, seed hair, xylem, phloem, parenchyma, endosperm, flowers, inflorescences, florets, peduncles, filaments, pedicles, anthers, pistils, stamen, sepal, receptacles, stigma, style, ovaries, ovules, pollen, spores, microspores, gametophytes, sporophytes, embryos, fruit, pods, seeds, grain, cotyledons, hypocotyls, epicotyls, calli, meristematic cells, companion cells, guard cells, protoplasts, tissues, cells, or any other organs, tissues, cells, subcellular components of a plant, or combinations thereof.

The term "plant product" as used herein refers to an agricultural or commercial product created from a plant, plant part, or seed. Non-limiting examples of plant products comprise flowers, pollen, leaves, vines, stalks, fruits, vegetables, cucurbits, roots, tubers, cones, pods, seeds, beans, grains, kernels, hulls, meals, grits, flours, sugars, starches, protein concentrates, protein isolates, waxes, oils, extracts, juices, concentrates, liquids, and syrups.

The term "progeny" as used herein refers to a first generation ($F_1$) plant.

The term "seeds per kilogram" as used herein refers to the number of seeds required to comprise 1 kilogram mass.

The term "seed yield" as used herein refers to the kilograms of seed produced in a hectare plot and is reported as kilograms per hectare (kg/ha). A hectare is 100 Ares and is equivalent to 10,000 $m^2$ or about 2.47 acres.

The term "sibbing," "sibbed," or "sib crossing" as used herein refers to the pollinating of an emasculated plant with pollen from a sister plant.

The term "Rehnborg" as used herein refers to the chia (Salvia hispanica L.) variety designated Rehnborg, a representative sample of seed having been deposited under ATCC Patent Deposit Designation PTA-124758.

The term "relative gain" as used herein refers to the percent increase in the mass of 1000 seeds as compared to other varieties.

The term "relative yield" as used herein refers to the percent increase in the mass of seeds per hectare as compared to other varieties.

The term "mass of 1000 seeds," "mass per one thousand seeds," or "MTS" as used herein refers to the mass of 1000 seeds in milligrams (e.g., mg/1000 seeds).

The term "nitrogen rate" as used herein refers to the quantity of nitrogen in kilograms applied to a cultivation locus. Nitrogen rate is typically reported as kilograms of nitrogen per hectare (kg N/ha).

The term "nitrogen use efficiency" or "NUE" as used herein is the ratio between the amount nitrogen assimilated by a population of plants and the amount of nitrogen applied to the plants (as fertilizer). NUE as used herein is calculated by obtaining the difference in seed yield (in kilograms) between plants administered nitrogen and those not administered nitrogen and dividing the difference by 100 kilograms of nitrogen: ((seed yield at $N_{100}$–seed yield at $N_0$)/100 kg N). Nitrogen use efficiency is reported as kg seed per kg of nitrogen fertilizer applied.

The term "wild-type" as used herein refers to the typical form of an organism or its genetic material, as it normally occurs, as distinguished from a selected organism. In one aspect, the wild-type is an undomesticated chia (Salvia hispanica L.) plant (or population thereof) or a domesticated chia plant (or population thereof) that has not undergone selection for agriculturally advantageous traits.

The term "yield gain for nitrogen applied" as used herein refers to the mass of seed obtained (in kilograms) per mass of nitrogen applied to the crop (e.g., kg seed/kg N).

The term "about" as used herein refers to any value that is within a variation of up to ±10% of the value modified by the term "about."

The article "a" or "an" as used herein means "one or more" unless otherwise specified.

The term "or" can be conjunctive or disjunctive.

Terms such as "include," "including," "contain," "containing," "have," "having," and the like mean "comprise" or "comprising."

Chia (Salvia hispanica L.) is an important and valuable crop for both food and agricultural products. A goal of chia breeding is to develop chia varieties that are genetically stable, high yielding, and have other agriculturally advantageous characteristics. Chia plants with such agriculturally advantageous traits can be selected, generated, crossed with other desirable varieties, and selected for enhanced agriculturally advantageous traits and hybrid vigor.

One embodiment described herein is a chia (Salvia hispanica L.) variety designated Rehnborg that has uniform white seeds, greater seed mass, and greater seed yields, compared to other typical chia varieties or wild-type chia. In one aspect, the chia (Salvia hispanica L.) variety designated Rehnborg comprises a chia plant or a chia seed, a representative sample of seed having been deposited under ATCC Patent Deposit Designation PTA-124758.

Another embodiment described herein is a method for selecting a chia (*Salvia hispanica* L.) plant comprising uniform seed color, increased seed mass, and enhanced seed yield. In one aspect, the Pinta variety was used as the progenitor line. A plurality of Pinta chia plants were planted and mass selection was conducted using white seed color as one selection characteristic. Improved seed weight was an indirect selection criterion that has been shown to be heritable. See Sosa et al., "Agronomic and physiological parameters related to seed yield of white chia (*Salvia hispanica* L.)," *Acta Fitogenetica* 3:31 (2016); and Sosa et al., "Plant traits related to seed yield and their heritability on white chia (*Salvia hispanica* L.)," *Acta Fitogenetica* 3:32 (2016). Two additional mass selections were performed in successive seasons. Three additional plant-by-plant selections were performed over three growing seasons. At the end of the first plant-by-plant selection, nearly uniform white seed was achieved. See Table 2, infra. The two additional plant-by-plant selections continued to produce 100% white seed. Basic seed was produced following the final plant-by-plant selection. See FIG. 1. This basic seed was designated as the chia (*Salvia hispanica* L.) Rehnborg variety, a representative sample of seed having been deposited under ATCC Patent Deposit Designation PTA-124758. The Rehnborg variety was produced solely using selection methods and did not encompass mutagenesis, transformation, or other molecular genetic manipulations. The Rehnborg variety of chia is considered a non-genetically modified organism (non-GMO).

Another embodiment described herein is a seed of chia (*Salvia hispanica* L.) variety designated Rehnborg. In one aspect, the chia seed has white color. In another aspect, the chia seed has an enhanced seed mass compared to similar chia varieties or wild-type seeds. In another aspect, the chia seed has an enhanced seed yield compared to similar chia varieties or wild-type seeds. In another aspect, the Rehnborg seed comprises an oil with a uniform pale color as compared to oil produced from black, brown, or mottled chia seed. Such oil is particularly suited for use in cosmetics or food where a uniform pale color is desirable and batch-to-batch consistency is important. Another aspect described herein is a uniform pale chia oil from the Rehnborg variety.

Another embodiment described herein is a chia (*Salvia hispanica* L.) plant of the Rehnborg variety comprising uniform white seed color, enhanced seed weight, enhanced seed yield, enhanced nitrogen fertilizer response, uniform days to flowering, and uniform days to maturity. In another aspect, the Rehnborg variety further comprises one or more of the following characteristics: increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants or wild type chia.

Another embodiment described herein is a chia (*Salvia hispanica* L.) plant variety designated Rehnborg. In one aspect, the plant can be obtained by planting a seed of chia (*Salvia hispanica* L.) variety designated Rehnborg in a growth medium and growing the plant. The medium can comprise soil, artificial soil, compost, culture media, hydroponic or hydroculture media, or any other suitable medium for growing plants.

Another embodiment described herein is a cell from a chia (*Salvia hispanica* L.) seed or chia plant from the variety designated Rehnborg. In one aspect, the cell comprises one or more cells or a tissue culture of cells from a Rehnborg variety plant or seed. One aspect described herein is a tissue culture of cells produced from a chia Rehnborg variety plant or plant part comprising an embryo, meristematic cell, leaf, cotyledon, hypocotyl, root, root tip, stem, pistil, anther, ovule, flower, pollen, or seed.

Another embodiment described herein is a chia plant regenerated from a cell or tissue culture derived from the Rehnborg variety, where the plant comprises the morphological and physiological characteristics of variety Rehnborg.

Another embodiment described herein is a chia plant or homogenous chia (*Salvia hispanica* L.) plant population comprising the Rehnborg variety. Such chia plant or plant population may be grown in a field, greenhouse, plant culture, aquaculture, or other means for growing plants. In one aspect, the population of Rehnborg variety can be obtained by planting a plurality of Rehnborg variety seeds in a suitable growth medium.

Another embodiment described herein is one or more chia seeds harvested from a plant or homogeneous population of plants of the Rehnborg variety.

Another embodiment described herein is a seed or homogenous population of chia (*Salvia hispanica* L.) seeds of the Rehnborg variety comprising white color. In one aspect, the chia seeds have a uniform white color. In another aspect, at least about 90%, about 91%, about 92%, about 9%3, about 94%, about 95%, about 96%, about 97%, about 98%, about 99%, or about 100% of the chia seeds have white color. In another aspect, at least about 90%-99%; about 95%-99%, about 98%-99%, about 90%-100%; about 95%-100%, about 98%-100%, or about 99%-100% of the chia seeds have white color. In another aspect, about 100% of the chia seeds have white color.

Another embodiment described herein is a seed or homogenous population of chia (*Salvia hispanica* L.) seeds of the Rehnborg variety comprising a high seed mass as compared to similar chia varieties or wild-type chia seeds. In one aspect, the Rehnborg chia seed has a mass of one thousand seeds of at least about 1400 mg/1000 seeds. In one aspect, the Rehnborg chia seed has a mass of one thousand seeds of at least about 1350 mg/1000 seeds. In another aspect, the Rehnborg chia seed has a mass of one thousand seeds of about 1350 mg/1000 seed, about 1360 mg/1000 seed, about 1370 mg/1000 seed, about 1380 mg/1000 seed, about 1390 mg/1000 seed, about 1400 mg/1000 seed, about 1410 mg/1000 seed, about 1420 mg/1000 seed, about 1430 mg/1000 seed, about 1440 mg/1000 seed, about 1450 mg/1000 seed, about 1460 mg/1000 seed, about 1470 mg/1000 seed, about 1480 mg/1000 seed, about 1490 mg/1000 seed, or about 1500 mg/1000 seed. In another aspect, the Rehnborg chia seed has a mass of one thousand seeds of about 1400 mg/1000 seed, about 1500 mg/1000 seed, about 1600 mg/1000 seed, about 1700 mg/1000 seed, about 1800 mg/1000 seed, about 1900 mg/1000 seed, 2000 mg/1000 seed, about 2100 mg/1000 seed, about 2200 mg/1000 seed, about 2300 mg/1000 seed, about 2400 mg/1000 seed, about 2500 mg/1000 seed, about 2600 mg/1000 seed, about 2700 mg/1000 seed, about 2800 mg/1000 seed, about 2900 mg/1000 seed, or about 3000 mg/1000 seed. In another aspect, the Rehnborg chia seed has a seed mass gain as compared to another chia seed of about 5%, about 6%, about 7%, about 8%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40% or about 50% over similar chia varieties or wild-type chia seeds.

Another embodiment described herein is a chia plant or homogenous population of chia (*Salvia hispanica* L.) plants of the Rehnborg variety comprising a high seed yield compared to similar chia varieties or wild-type chia plants. In one aspect, the Rehnborg variety has an average seed yield of at least about 1500 kilograms of seed per hectare (kg/ha). In another aspect, the Rehnborg variety has an average seed yield of about 1850 kg/ha. In another aspect, the Rehnborg variety has an average seed yield of about 2250 kg/ha. In another aspect, the Rehnborg variety has an average seed yield of about 3000 kg/ha. In another aspect, the Rehnborg variety has an average seed yield of about 1500 kg/ha to about 3000 kg/ha. In another aspect, the Rehnborg variety has an average seed yield of about 1850 kg/ha to about 3000 kg/ha. In another aspect, the Rehnborg variety has an average seed yield of about 2250 kg/ha to about 3000 kg/ha. In another aspect, the Rehnborg variety has an average seed yield of about 1500 kg/ha, about 1600 kg/ha, about 1700 kg/ha, about 1800 kg/ha, about 1900 kg/ha, about 2000 kg/ha, about 2100 kg/ha, about 2200 kg/ha, about 2300 kg/ha, about 2400 kg/ha, about 2500 kg/ha, about 2600 kg/ha, about 2700 kg/ha, about 2800 kg/ha, about 2900 kg/ha, about 3000 kg/ha, about 3100 kg/ha, about 3200 kg/ha, about 3300 kg/ha, about 3400 kg/ha, about 3500 kg/ha, about 3600 kg/ha, about 3700 kg/ha, about 3800 kg/ha, about 3900 kg/ha, about 4000 kg/ha, or about 5000 kg/ha. In another aspect, the Rehnborg variety has an average seed yield gain of about 10% to about 200% over similar chia varieties or wild-type chia. In another aspect, the Rehnborg variety has an average seed yield gain of about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, or about 150% over similar chia varieties or wild-type chia. In another aspect, the Rehnborg variety has an enhanced average seed yield in the fall-winter growing season. In another aspect, the Rehnborg variety has an enhanced average seed yield in the winter-spring growing season. In another aspect, the Rehnborg variety has an enhanced average seed yield in the spring-summer growing season. In another aspect, the Rehnborg variety has an enhanced average seed yield in the summer-fall growing season. In another aspect, the Rehnborg variety has an enhanced average seed yield throughout the year.

Another embodiment described herein is a homogenous population of chia (*Salvia hispanica* L.) plants of the Rehnborg variety comprising a high uniformity in time to flowering and maturity. In one aspect, the Rehnborg variety begins flowering at about 55 days after sowing and ends flowering about 63 days after sowing; this corresponds to a flowering period of about 8 days. In contrast, other chia varieties have flowering periods of 10 to 16 days. In another aspect, the Rehnborg variety begins reaching maturity at about 111 days after sowing and ends maturity at about 120 days after sowing; this corresponds to a period of about 9 days. In contrast, other chia varieties have flowering periods of 8 to 15 days. Such uniformity exhibited by the Rehnborg variety permits the plants to evade damage caused by predators such as birds and reduce seed losses during harvest.

Another embodiment described herein is a chia (*Salvia hispanica* L.) plant or homogenous plant population of the Rehnborg variety comprising an enhanced fertilizer response. In one aspect, the Rehnborg variety has a nitrogen use efficiency (NUE) of about 11.2 kg of seed per kg of nitrogen fertilizer applied. In one aspect, the Rehnborg variety has a nitrogen use efficiency (NUE) of about 10 kg to about 20 kg of seed per kg of nitrogen fertilizer applied. In another aspect, the Rehnborg variety produces at least about 10 kg of seed per kg of nitrogen fertilizer applied. In another aspect, the Rehnborg variety produces about 10 kg to about 15 kg of seed per kg of nitrogen fertilizer applied. In another aspect, the Rehnborg variety produces about 10 kg, about 11 kg, about 12 kg, about 13 kg, about 14 kg, about 15 kg, about 16 kg, about 17 kg, about 18 kg, about 19 kg, or about 20 kg of seed per kg of nitrogen fertilizer applied. In another aspect, the Rehnborg variety has an average seed yield gain of at least about 1120 kg when fertilized with 100 kg of nitrogen per hectare. In another aspect, the Rehnborg variety has an average seed yield gain of about 750 kg, about 800 kg, about 850 kg, about 900 kg, about 950 kg, about 1000 kg, about 1100 kg, about 1200 kg, about 1300 kg, about 1400 kg, about 1500 kg, about 1600 kg, about 1700 kg, about 1800 kg, about 1900 kg, or about 2000 kg when fertilized with 100 kg of nitrogen per hectare.

Another embodiment described herein is a plant product produced from chia seed harvested from a plant or homogeneous plant population comprising the Rehnborg variety. The plant product comprises one or more of chia seeds, oil, meal, protein, fiber, derivatives thereof, or combinations thereof. In one aspect, the plant product comprises chia seeds, chia oil, or chia meal. In one aspect, the plant product comprises chia oil. In one aspect, the chia oil has high concentrations of omega-3 polyunsaturated fatty acids. In another aspect, the chia oil has a uniform pale color. As described herein, the Rehnborg variety has enhanced seed mass and yields as compared to similar chia varieties or wild-type chia. Accordingly, the yields of Rehnborg variety plant products, particularly seed products such as oil or meal is greater than similar chia varieties or wild-type chia. Another aspect described herein is a cosmetic or beauty product produced using chia oil from the Rehnborg variety. Another aspect described herein is a food product comprising chia seed, chia meal, chia oil, a derivative thereof, or a combination thereof from the Rehnborg variety. Another aspect described herein is bulk chia seed from the Rehnborg variety.

Another embodiment described herein is a crop population of plants of the Rehnborg variety. In one aspect, the crop may be grown in a field, greenhouse, plant culture, hydroponic array, or other suitable growing area. In another aspect, the crop may be sown in one environment and then transplanted to another environment. For example, seeds may be sown and germinated in a greenhouse environment and then seedlings or immature plants transplanted to a field for growth until maturity or harvest.

Another embodiment described herein is a plant part of a chia (*Salvia hispanica* L.) plant from the variety designated Rehnborg. In one aspect, the plant part is a seed.

Another embodiment described herein is a descendant of a chia (*Salvia hispanica* L.) seed or chia plant from the variety designated Rehnborg, the descendant comprising the traits and physiological and morphological characteristics of chia (*Salvia hispanica* L.) variety Rehnborg. The Rehnborg descendant may be a descendant plant or a seed of a descendant plant. In one aspect, the Rehnborg descendant comprises one or more traits comprising increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants. In one aspect, the descendant is an $F_1$, $F_2$, $F_3$, $F_4$, $F_5$, $F_6$, $F_7$, $F_8$, $F_9$, $F_{10}$, or later generation of the Rehnborg variety. In another embodiment, the descendant is a backcross descendant of the Rehnborg variety. Another aspect described herein is a seed from a descendant from the variety designated Rehnborg, comprising the traits and physiological and morphological characteristics of chia (*Salvia hispanica* L.) variety Rehnborg.

Another embodiment described herein is germplasm of chia (*Salvia hispanica* L.) variety designated Rehnborg. One aspect described herein is a chia plant generated from the Rehnborg germplasm comprising the traits and physiological and morphological characteristics of chia (*Salvia hispanica* L.) variety Rehnborg. In one aspect, a plant is generated from the germplasm and comprises one or more traits comprising increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants. In another aspect, one or more seeds are obtained from the germplasm-generated plant comprising the traits and physiological and morphological characteristics of the Rehnborg variety.

Another embodiment described herein is a method for producing one or more Rehnborg variety chia seeds. In one aspect, the method for producing Rehnborg seed comprises: (a) planting a seed of the Rehnborg variety in pollinating proximity to itself or to a seed from a different chia variety; (b) growing a plant from the seeds planted in pollinating proximity; and harvesting one or more resultant chia seeds. Another aspect described herein is a chia seed produced by the foregoing method comprising the traits and physiological and morphological characteristics of chia (*Salvia hispanica* L.) variety Rehnborg.

Another embodiment described herein is a method for producing a chia (*Salvia hispanica* L.) variety plant by crossing a first parent chia (*Salvia hispanica* L.) plant with a second parent chia (*Salvia hispanica* L.) plant where either the first or second parent chia plant is a chia plant of the line Rehnborg. In another aspect, both the first and second parent chia (*Salvia hispanica* L.) plants can be of the variety Rehnborg or descendants thereof. Any such methods using chia (*Salvia hispanica* L.) variety Rehnborg may be employed including selfing, backcrosses, hybrid production, crosses to populations, and the like. This comprises all plants or seeds thereof produced using chia (*Salvia hispanica* L.) variety Rehnborg as at least one parent, including those developed from varieties derived from or descendant from chia (*Salvia hispanica* L.) variety Rehnborg. Advantageously, this chia (*Salvia hispanica* L.) variety can be used in crosses with other, different, chia (*Salvia hispanica* L.) plants to produce the first generation ($F_1$) chia (*Salvia hispanica* L.) hybrid seeds and plants with superior characteristics.

Another embodiment described herein is a method for producing a variety Rehnborg-derived chia (*Salvia hispanica* L.) plant by crossing variety Rehnborg with a second chia (*Salvia hispanica* L.) plant that comprises one or more agriculturally advantageous traits, obtaining seed from the resulting progeny; growing the progeny seed, and repeating the crossing and growing steps with the variety Rehnborg-derived plant from 1 to 20 times. Another aspect described herein is the plants or seed produced from the foregoing methods or processes, comprising the traits and physiological and morphological characteristics of chia (*Salvia hispanica* L.) variety Rehnborg and any other agriculturally advantageous traits from the second chia plant.

Another embodiment described herein is a method for producing a chia (*Salvia hispanica* L.) variety Rehnborg seed, the method comprising: (a) crossing a chia (*Salvia hispanica* L.) variety Rehnborg plant with a second different chia (*Salvia hispanica* L.) variety Rehnborg plant to produce $F_1$ chia seed; and (b) harvesting the $F_1$ chia seed. Another aspect described herein is a chia seed produced by the foregoing method comprising the traits and physiological and morphological characteristics of chia (*Salvia hispanica* L.) variety Rehnborg.

Another embodiment described herein is a method of using the variety Rehnborg in selfing, backcrosses, hybrid production, crosses to populations, and similar procedures. Also described herein are plants or seeds produced using variety Rehnborg as a parent, including plants descendant from or derived from variety Rehnborg comprising the traits and physiological and morphological characteristics of chia (*Salvia hispanica* L.) variety Rehnborg. Advantageously, the Rehnborg variety is used in crosses with other, different, varieties to produce first generation ($F_1$) chia (*Salvia hispanica* L.) seeds and plants with superior agricultural characteristics.

Another embodiment described herein is a method of introducing a desired trait into chia (*Salvia hispanica* L.) variety Rehnborg. In one aspect described herein, the method comprises: (a) crossing a Rehnborg plant with a plant of another, different chia (*Salvia hispanica* L.) variety that comprises one or more agriculturally advantageous traits to produce $F_1$ progeny plants; (b) selecting one or more progeny plants that have the desired trait to produce selected progeny plants; (c) crossing the selected progeny plants with the Rehnborg plants to produce backcross progeny plants; (d) selecting for backcross progeny plants that have the desired trait; and (e) repeating steps (c) and (d) three or more times in succession to produce fourth or higher backcross progeny plants that comprise the desired trait. Another aspect described herein is a chia plant or a seed from such plant produced by the foregoing method comprising the traits and physiological and morphological characteristics of chia (*Salvia hispanica* L.) variety Rehnborg and one or more desired traits. The desired trait can comprise increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants.

Reproduction of the Rehnborg variety can occur by natural processes, tissue culture, or regeneration. As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture. Means for preparing and maintaining plant tissue culture are well known in the art. Tissue culture comprising plant organs has been used to produce regenerated plants. See e.g., U.S. Pat. Nos. 5,959,185; 5,973,234; and 5,977,445, the disclosures of which are incorporated herein by reference.

Tissue culture of various tissues of chia (*Salvia hispanica* L.) and regeneration of plants therefrom is known within the art. See e.g., Teng et al., *HortScience* 27(9): 1030-1032 (1992); Teng et al., *HortScience* 28(6):669-1671 (1993); Zhang et al., *J. Gen. Breeding* 46(3): 287-290 (1992); Webb et al., *Plant Cell Tissue Organ Culture* 38(1): 77-79 (1994); Curtis et al., *J. Exp. Botany* 45(279): 1441-1449 (1994); Nagata et al., *J. Amer. Soc. Horticult. Sci.* 125(6): 669-672 (2000); Ibrahim et al., *Plant Cell Tissue Organ Culture* 28(2): 139-145 (1992).

Another embodiment described herein is one or more cells that can be grown and differentiated to produce chia (*Salvia hispanica* L.) plants having the physiological and morphological characteristics of variety Rehnborg. Another aspect described herein is chia seed produced from such tissue-culture derived plants having the physiological and morphological characteristics of variety Rehnborg. Other aspects described herein are chia plants derived from or descendant from tissue-culture derived plants having the physiological and morphological characteristics of variety Rehnborg.

Another embodiment described herein is the transformation of the Rehnborg variety with exogenous genes to impart new or enhanced agriculturally advantageous traits using protocols known to those of skill in the art. Another aspect described herein is the culture, plants, or seed produced from the transformation, comprising the traits and physiological and morphological characteristics of variety Rehnborg and any other agriculturally advantageous traits.

Another embodiment described herein is a method for developing novel chia (*Salvia hispanica* L.) plants or seeds based on the Rehnborg variety. In one embodiment, the specific type of breeding method is pedigree selection, where both single plant selection and mass selection practices are employed. Pedigree selection is described by Walter R. Fehr, *Principles of Cultivar Development*, Macmillan Pub. Co. (1993), which is incorporated by reference herein for such teachings.

Chia (*Salvia hispanica* L.) plants may be selected for agriculturally advantageous characteristics. In one embodiment, the pedigree method of breeding is practiced where selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny row as the preceding generation.

Using the pedigree method, two parents may be crossed using an emasculated female and a pollen donor (male) to produce $F_1$ offspring or open pollination. Methods of removing pollen, such as misting to wash the pollen off prior to fertilization, may be employed to assure crossing or hybridization. The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

In addition to crossing, selection may be used to identify and isolate new chia (*Salvia hispanica* L.) lines comprising agriculturally advantageous characteristics. In chia (*Salvia hispanica* L.) selection, chia seeds are planted, the plants are grown, and single plant selections are made of plants with desired characteristics. Seed from the single plant selections may be harvested, separated from seeds of the other plants in the field, and re-planted. The plants from the selected seed may be monitored to determine whether they exhibit the desired characteristics of the originally selected line. Selection work is preferably continued over multiple generations to increase the uniformity of the new line.

The choice of a breeding or selection method depends on the mode of plant reproduction, the heritability of the trait(s) being improved, and the type of variety used commercially (e.g., $F_1$ hybrid variety, pure line variety, etc.). For highly heritable traits, the evaluation of superior individual plants evaluated at a single location will be effective; whereas for traits with low heritability, selection should be based on mean values obtained from replicated evaluations of families of related plants, typically grown at different locations to normalize for environmental factors. Popular selection methods commonly include pedigree selection, modified pedigree selection, mass selection, and recurrent selection.

The complexity of inheritance influences choice of the breeding method. Backcross breeding may be used to transfer one or more agriculturally advantageous traits into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria may vary depending on the goal and objectives, but should include gain from selection per year based on comparisons to an appropriate standard, the overall value of the advanced breeding lines, and the number of successful varieties produced per unit of input (e.g., per year, per dollar expended, etc.).

In another embodiment, promising advanced breeding lines are thoroughly tested and compared to appropriate standards in environments representative of the commercial target area(s). The best lines are candidates for new commercial varieties; those deficient in a few traits can be used as parents to produce new populations for further selection.

These processes, which lead to the final step of marketing and distribution, usually take several years from the time the first cross or selection is made. Therefore, development of new varieties is a time-consuming process that requires precise forward planning, efficient use of resources, and adherence to the planned process.

The identification of individual plants that are genetically superior can be difficult, because for most traits, the true genotypic value may be masked by other confounding plant traits or environmental factors. One method for identifying superior plants is to observe their performance relative to other experimental plants and to a widely grown standard variety. If a single observation is inconclusive, replicated observations provide a better evaluation of the genetic worth.

The goal of chia (*Salvia hispanica* L.) plant breeding is to develop new, unique, and superior chia (*Salvia hispanica* L.) varieties having one or more agriculturally advantageous characteristics. In one embodiment, two or more parental lines are crossed, followed by repeated selfing and selection, producing many new genetic combinations. Millions of different genetic combinations can be generated via crossing, selfing, and mutations. Each year germplasm is selected to advance to the next generation. This germplasm may be grown under different geographical, climatic, and soil conditions, and further selections are then made during and at the end of the growing season.

In another embodiment, the development of commercial chia (*Salvia hispanica* L.) varieties requires the development of chia (*Salvia hispanica* L.) varieties, the crossing of these varieties, and the evaluation of the crosses for agriculturally advantageous characteristics. Pedigree breeding and recurrent selection breeding methods may be used to develop varieties from breeding populations. Breeding programs may combine desirable traits from two or more varieties or various broad-based sources into breeding pools from which varieties are developed by selfing and selection of desired phenotypes. The new varieties may be crossed with other varieties and the hybrids from these crosses are evaluated to determine which have commercial potential.

Another embodiment described herein is a method for developing variety Rehnborg progeny chia (*Salvia hispanica* L.) plants in a chia plant breeding program comprising: obtaining a chia (*Salvia hispanica* L.) plant, or a part thereof, of variety Rehnborg, utilizing the plant or plant part as a source of breeding material, and selecting a chia (*Salvia hispanica* L.) variety Rehnborg progeny plant with molecular markers in common with variety Rehnborg and/or with morphological and/or physiological characteristics listed in Table 3 or described herein. Such characteristics can comprise one or more of increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants. Breeding steps that may be used in the chia (*Salvia hispanica* L.) plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another embodiment described herein is a method producing a population of chia (*Salvia hispanica* L.) variety Rehnborg-progeny chia (*Salvia hispanica* L.) plants, comprising crossing variety Rehnborg with another chia (*Salvia hispanica* L.) plant, thereby producing a population of chia (*Salvia hispanica* L.) plants, which, on average, derive 50% of their alleles from chia (*Salvia hispanica* L.) variety Rehnborg. A plant of this population may be selected and repeatedly selfed or sibbed with a chia (*Salvia hispanica* L.) variety resulting from these successive filial generations. One embodiment is the chia (*Salvia hispanica* L.) variety produced by this method that has obtained at least 50% of its alleles from chia (*Salvia hispanica* L.) variety Rehnborg and having the physiological and morphological characteristics of variety Rehnborg.

Another embodiment described herein is chia (*Salvia hispanica* L.) variety Rehnborg progeny plants comprising a combination of one or more variety Rehnborg traits comprising any of those listed in Table 3 or described herein, so that the progeny chia plant is not significantly different for the traits than chia (*Salvia hispanica* L.) variety Rehnborg as determined at the 5% significance level when grown in the same environmental conditions. Using techniques described herein, molecular markers may be used to identify the progeny plant as a chia (*Salvia hispanica* L.) variety Rehnborg progeny plant. Mean trait values may be used to determine whether trait differences are significant, and preferably, the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of chia (*Salvia hispanica* L.) variety Rehnborg may also be characterized through their filial relationship with chia (*Salvia hispanica* L.) variety Rehnborg, as for example, being within a certain number of breeding crosses of chia (*Salvia hispanica* L.) variety Rehnborg. A breeding cross is a cross intended to introduce new genetics into the progeny, and is distinguished from a cross, such as a self or a sib cross, made to select among existing genetic alleles. The lower the number of breeding crosses in the pedigree, the closer the relationship between chia (*Salvia hispanica* L.) variety Rehnborg and its progeny. Progeny produced by the methods described herein may be within 1, 2, 3, 4, or 5 crosses of chia (*Salvia hispanica* L.) variety Rehnborg.

Breeding methods that are used for selecting agriculturally advantageous characteristics or traits in crops are known in the art. See Robert W. Allard, *Principles of Plant Breeding*, $2^{nd}$ ed. John Wiley and Son, (2010), which is incorporated by reference herein for such teachings. The following breeding methods may be used with chia (*Salvia hispanica* L.) variety Rehnborg in the development of further chia (*Salvia hispanica* L.) plants.

Pedigree breeding is used commonly for the improvement of self-pollinating crops or inbred lines of cross-pollinating crops. Two parents comprising favorable, complementary traits are crossed to produce an $F_1$. An $F_2$ population is produced by selfing one or several $F_1$s or by intercrossing two $F_1$s (sibling mating). Selection of the best individuals typically occurs in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (e.g., $F_6$ and $F_7$), the best lines, or mixtures of phenotypically similar lines are tested for potential release as new varieties.

Mass and recurrent selections can be used to improve populations of either self- or cross-pollinating crops. A genetically variable population of heterozygous individuals may be identified or created by intercrossing several different parents. The best plants may be selected based on individual superiority, outstanding progeny, or excellent combining ability. Preferably, the selected plants are intercrossed to produce a new population comprising agriculturally advantageous characteristics in which further cycles of selection are continued.

Backcross breeding has been used to transfer genes for a simply inherited, highly heritable trait into a desirable homozygous variety or line that is the recurrent parent. The source of the trait to be transferred is called the donor parent. The resulting plant is expected to have the attributes of the recurrent parent (e.g., variety) and the desirable trait transferred from the donor parent. After the initial cross, individuals possessing the phenotype of the donor parent may be selected and repeatedly crossed (backcrossed) to the recurrent parent. The resulting plant is expected to have the attributes of the parent and the desirable traits transferred from the donor parent.

The single-seed descent procedure refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advancement is completed.

In a multiple-seed procedure, one or more seeds from each plant in a population is harvested and combined together to form a bulk. Part of the bulk is used to plant the next generation and part is put in reserve. The procedure has been referred to as modified single-seed descent or the pod-bulk technique. The multiple-seed procedure conserves time and labor resources at harvest. It is considerably faster to obtain bulk seed than to select single seeds from each by hand. The multiple-seed procedure facilitates planting the same number of seeds from a population for each generation of inbreeding. Enough seeds are harvested to compensate for plants that did not germinate or produce seed.

Mutation breeding is a method for introducing new agriculturally advantageous characteristic into chia (*Salvia hispanica* L.) varieties. Spontaneous mutations or those artificially induced are useful sources of variability. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, acridines, or other mutagens. Once a desired trait is observed through mutagenesis the trait may then be incorporated into existing germplasm by traditional breeding techniques. Protocols for mutation breeding can be found in Walter R. Fehr, *Principles of Cultivar Development*, Macmillan Pub. Co. (1993), which is incorporated by reference for such teachings.

Another embodiment described herein is the mutagenesis of the Rehnborg variety with chemical mutagens or ionizing radiation to induce one or more mutations and then selecting for one or more agriculturally advantageous traits by methods known in the art. For example, seeds of Rehnborg variety could be treated with chemical mutagens, planted, and then the resulting plants selected for an agriculturally advantageous trait, such as herbicide tolerance, cold tolerance, drought tolerance, or insect resistance.

The production of double haploids can also be used for the development of homozygous varieties in a breeding program. Double haploids are produced by the doubling of a set of chromosomes from a heterozygous plant to produce a completely homozygous individual. See Wan et al., "Efficient production of doubled haploid plants through colchicine treatment of anther-derived maize callus," *Theor. Appl. Genet.*, 77:889-892 (1989), which is incorporated by reference.

It will be readily apparent to one of ordinary skill in the relevant arts that suitable modifications and adaptations to the compositions, methods, and applications described herein can be made without departing from the scope of any embodiments or aspects thereof. The plant varieties, seeds, compositions, processes, and methods provided are exemplary and are not intended to limit the scope of any of the specified embodiments. All of the various embodiments, aspects, and options disclosed herein can be combined in any variations or iterations. The scope of all plant varieties, seeds, hybrids, crosses, compositions, formulations, methods, and processes described herein include all actual or potential combinations of embodiments, aspects, options, examples, and preferences herein described. All patents, publications, and non-patent literature cited herein are incorporated by reference herein for the specific teachings thereof. The citation of any references herein is not an admission that such references are prior art. If any material incorporated by reference contradicts or is inconsistent with this specification, the specification will supersede any such material.

EXAMPLES

Example 1

Multiple chia (*Salvia hispanica* L.) varieties outlined in Table 1 were evaluated for color uniformity and seed yields. The chia (*Salvia hispanica* L.) Rehnborg variety described herein is shown in the penultimate row for comparison. Three chia varieties had uniform seed color: Black Puebla, Heartland, and Sahi Alba 914.

TABLE 1

Seed color, uniformity of seed color, and seed mass of chia (*Salvia hispanica* L.) collected from different regions of Mexico and the USA

| Origin | Seed Color | Color (%) | MTS* (mg) | Breeding Rights |
|---|---|---|---|---|
| Tuxpan, Jalisco | Black | 84 | 1050 | None |
| Sunnyside, WA | Black | 85 | 1178 | None |
| Jojutla, Morelos | Black | 88 | 1145 | None |
| Navojoa, Sonora | Black | 88 | 1209 | None |
| Tepoztlan, Morelos | Black | 89 | 1125 | None |
| Texcoco, Mexico | Black | 89 | 840 | None |
| Acatic, Jalisco | Black | 92 | 1235 | None |
| Acatic, Jalisco | White | 96 | 1275 | None; Chiablanca SC de RL |
| Atlixco, Puebla | Black | 100 | 1324 | None; possibly Black Puebla |
| Olinala, Guerrero | Black | 100 | 1215 | None; possibly Black Puebla |
| Lauderdale, FL | Black | 100 | 1275 | None; possibly Black Puebla |
| Sahi Alba 914 | White | 100 | 1234 | TFSB, LLC, DE US |

TABLE 1-continued

Seed color, uniformity of seed color, and seed mass of chia (*Salvia hispanica* L.) collected from different regions of Mexico and the USA

| Origin | Seed Color | Color (%) | MTS* (mg) | Breeding Rights |
|---|---|---|---|---|
| Heartland | White | 100 | 1287 | Heartland |
| Heartland | Black | 100 | 1257 | Heartland |
| Rehnborg | White | 100 | 1427 | |

MTS: mass per one thousand seeds

Black Puebla is an inbreed chia variety that is cultivated in the agricultural regions of Puebla, Mexico. See Muñoz, "Capital social y empresa rural, una visión rural desde México; el caso de una empresa productora de chia orgánica," *Nueva Antropologia* 25(77): 15-30 (2012).

The Heartland variety was developed by the University of Kentucky Research Foundation, Lexington, Ky., USA and is described in U.S. Pat. No. 8,586,831. There are two presentations of Heartland; one has uniform black seeds and the other uniform white seeds.

The Sahi Alba 914 variety was developed in Argentina by TFSB LLC, Dover, Del., USA and is described in U.S. Pat. No. 9,686,926.

Example 2

Rehnborg Variety Selection

The Rehnborg chia (*Salvia hispanica* L.) variety described herein was developed at Rancho El Petacal farm in Jalisco, Mexico. This variety has high white seed color uniformity (e.g., 100% white seeds). The Rehnborg variety also has higher seed mass (mass per thousand seeds: 1427 mg) as compared with the Heartland (1234 mg) and Sahi Alba 914 (1287 mg) varieties.

The Rehnborg variety was generated after six cycles of selection, beginning with the Pinta variety, using seed color as one of the selection criteria. Table 2 outlines the selection process. FIG. 1 shows the progression of seed color uniformity during the selection process.

TABLE 2

Breeding selection for the Rehnborg variety

| Selection | Year | Breeding Method | Plant population screened | Plants selected | White seed (%) |
|---|---|---|---|---|---|
| 1 | 2010 SF | Mass selection | 1300 | 104 | 8 |
| 2 | 2011 SF | Mass selection | 1300 | 910 | 70 |
| 3 | 2012 SF | Mass selection | 1300 | 1170 | 90 |
| 4 | 2013 SF | Plant by plant | 1300 | 39 | 98 |
| 5 | 2014 WS | Plant by plant | 897 | 39 | 99 |
| 6 | 2015 SF | Plant by plant | 897 | 23 | 100 |
| 7 | 2015 WS | Basic seed | 1300 | 1300 | 100 |

Selections 1-4 were grown during the Summer-Fall seasons; cycles 5-7 were grown during the 2104 Winter-Spring season, 2015 Summer-Fall season, and 2015 Winter-Spring season, respectively.

Figure 9:
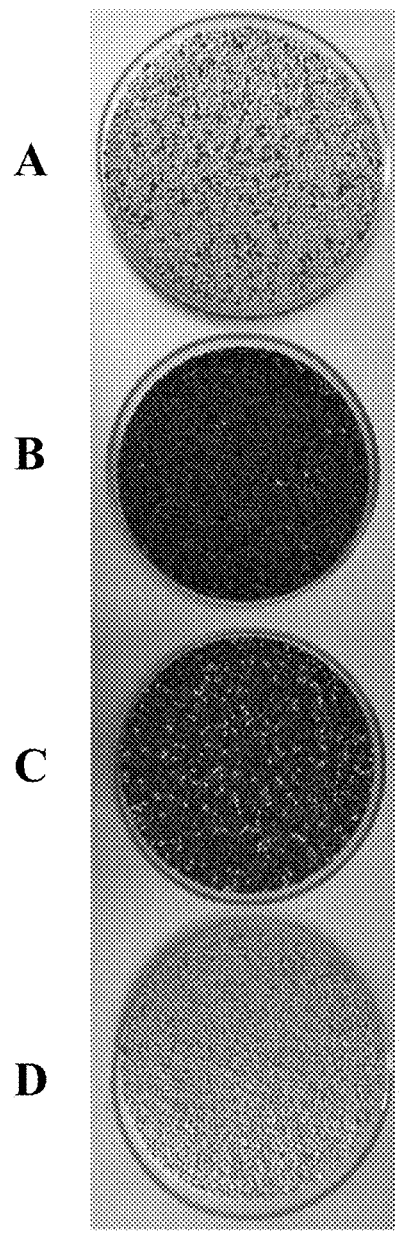
FIG. 9. Seed color and uniformity of four varieties of chia. The planting date was Jul. 15, 2017 and samples were obtained on Nov. 30, 2017 (137 days after sowing). (A) White Acatic; (B) Black Puebla; (C) Pinta; (D) Rehnborg.
Figure 10:
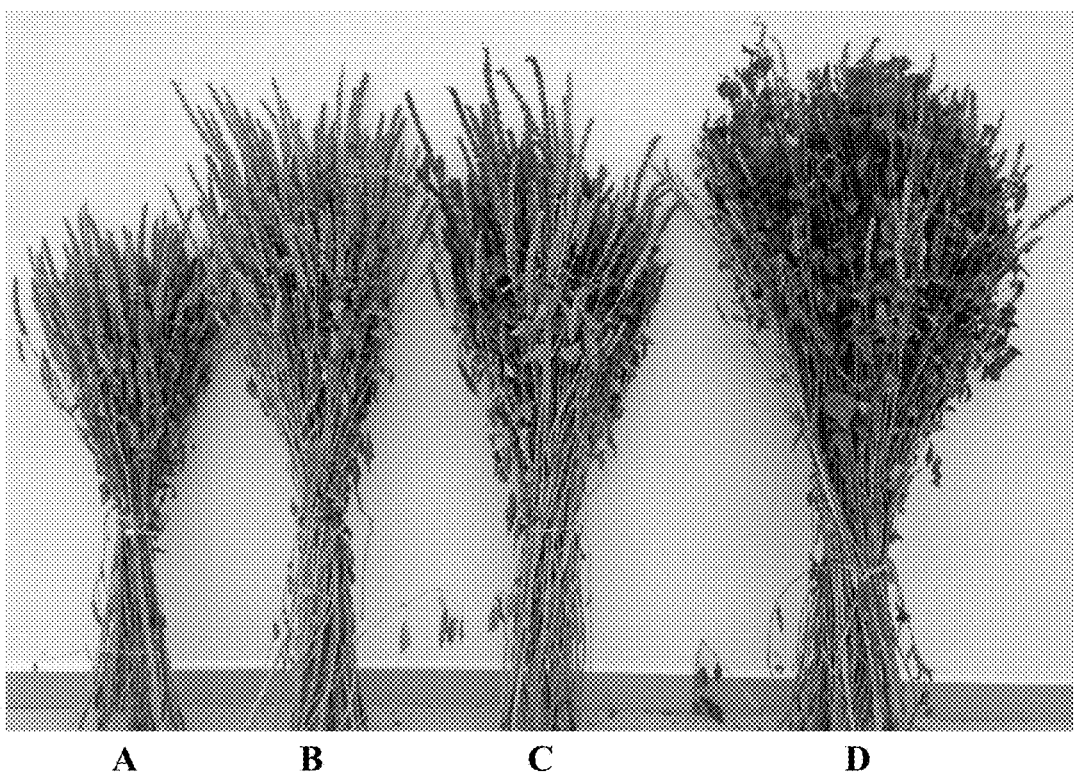
FIG. 10. Development of four varieties of chia during the Winter-Spring season. Plants were sown on Jan. 20, 2017 at Rancho El Petacal, Jalisco, Mexico and harvested on May 15, 2017 (114 days after sowing). (A) White Acatic; (B) Rehnborg; (C) Pinta; (D) Black Puebla. The Black Puebla and Pinta varieties (D and C) did not reach physiological maturity. Data is shown in Table 7.

During the last three cycles of selecting plant by plant, the main inflorescences (the complete flower head of the plant including stems, stalks, and flowers) were covered to avoid pollination by insects; therefore, no out-crossing was performed with the plants selected. In addition, the basic seed was increased in a greenhouse to eliminate the presence of natural pollinators. This process resulted in near complete seed color uniformity within five selection cycles. The last two selection cycles produced seed that was 100% white (Table 2, FIG. 1; FIG. 9).

Variety Description

The Rehnborg chia (*Salvia hispanica* L.) variety, a representative sample of seed having been deposited under ATCC Patent Deposit Designation PTA-124758, was observed to possess the following morphological and physical characteristics, based on the average of 10 observations conducted at Rancho El Petacal farm in Jalisco, Mexico during the 2017 Summer-Fall growing season. Data for Pinta (the progenitor variety), White Acatic, and Black Puebla are shown for comparison and were grown during the same season under similar conditions.

TABLE 3

Rehnborg variety description information and comparative data

| Characteristic* | Rehnborg | Pinta | White Acatic | Black Puebla |
|---|---|---|---|---|
| Flowering (days after sowing) | 58 | 58 | 55 | 65 |
| Maturity (days after sowing) | 115 | 115 | 105 | 125 |
| Mature plant height (mm) | 1760 | 1750 | 1370 | 1750 |
| Main stem length (mm) | 1450 | 1520 | 1100 | 1440 |
| Stem diameter (base) (mm) | 6 | 6 | 5 | 6 |
| Nodes per plant | 10 | 9 | 9 | 11 |
| Inflorescence per plant | 8 | 6 | 8 | 8 |
| Branches per plant | 8 | 6 | 6 | 8 |
| Leaf width (mm) | 68 | 68 | 60 | 70 |
| Leaf length (mm) | 123 | 120 | 115 | 110 |
| Length of petiole (mm) | 60 | 55 | 34 | 50 |

TABLE 3-continued

Rehnborg variety description information and comparative data

| Characteristic* | Rehnborg | Pinta | White Acatic | Black Puebla |
|---|---|---|---|---|
| Main inflorescence length (mm) | 250 | 150 | 190 | 240 |
| Main inflorescence height (mm)† | 1510 | 1610 | 1180 | 1520 |
| Cluster per inflorescence | 30 | 26 | 23 | 24 |
| Florets per cluster | 10 | 9 | 13 | 13 |
| Petal colors | Purple | Purple | Purple | Blue |
| Flower length (mm) | 13 | 11 | 11 | 9 |
| Calix length (mm) | 7 | 7 | 8 | 6 |
| Corolla length (mm) | 6 | 4 | 3 | 3 |
| Petals per floret | 1 | 1 | 1 | 1 |
| Anthers per floret | 2 | 2 | 2 | 2 |
| Stigmas per floret | 1 | 1 | 1 | 1 |
| Seeds per fruit | 4 | 4 | 4 | 4 |
| Seed color | 100% white | 90% black | 96% white | 100% black |
| Mass per 1000 seeds (mg) | 1453 | 1320 | 1245 | 1344 |
| Seed yield (kg/ha) | 1856 | 1062 | 1400 | 983 |

*Results are mean values obtained from the observation of 10 individual plants.
†Height from ground level.

Figure 2:
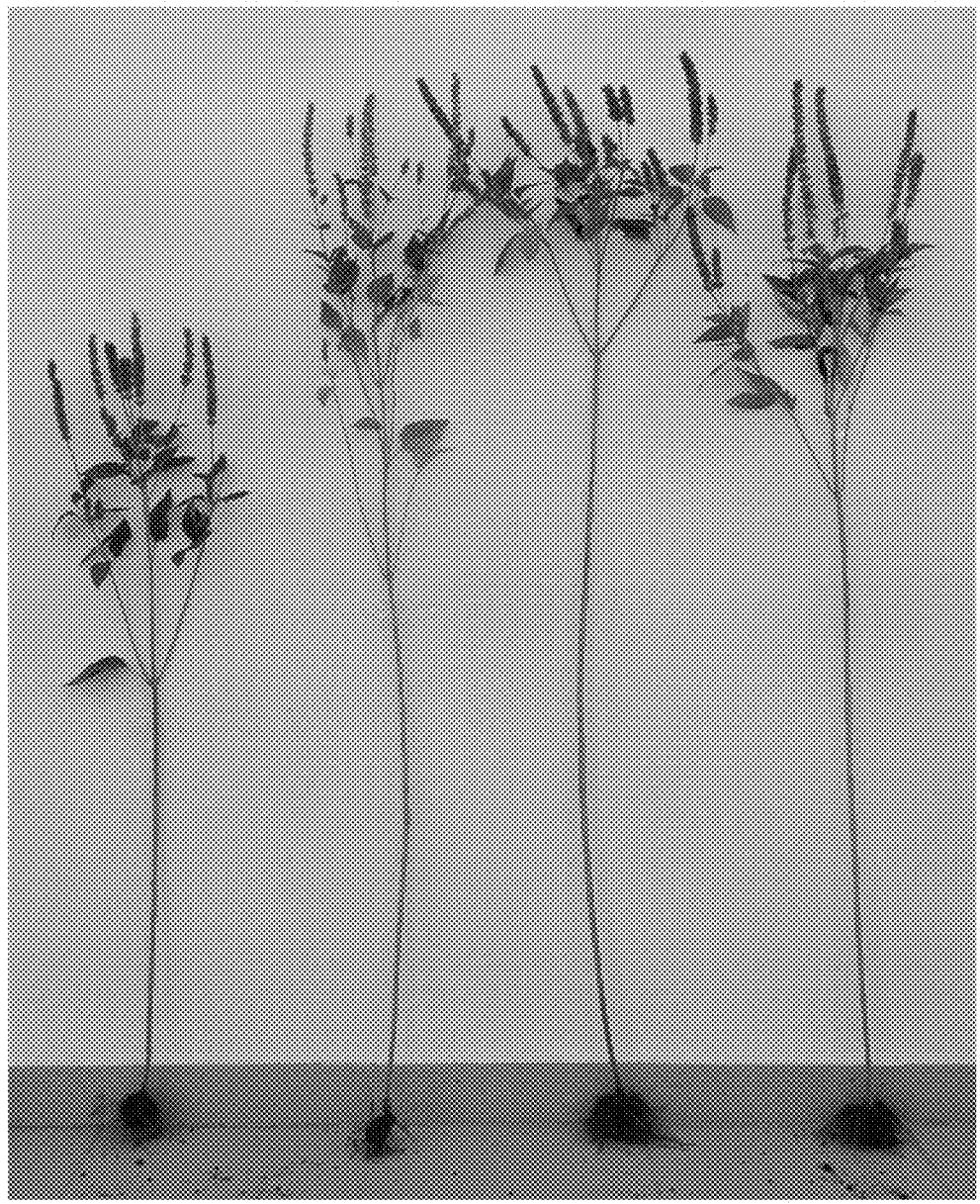
FIG. 2. Plant heights of four varieties of chia. Plants were planted on Aug. 15, 2017 and samples were obtained on Nov. 30, 2017, which is 107 days after sowing. (A) White Acatic; (B) Black Puebla; (C) Pinta; (D) Rehnborg. Table 3 lists results for the physical and morphological characteristics shown in FIGS. 2-9. All samples shown in FIGS. 2-9 were grown at Rancho El Petacal, Jalisco, Mexico during the Summer-Fall season from Jul. 15, 2017 to Nov. 30, 2017.
Figure 3:
FIG. 3. Inflorescence length at flowering stage (right) and physiologically mature stage (left) of four varieties of chia. The planting date for the flowering stage was Sep. 15, 2017 and Aug. 15, 2017 for the physiologically mature stage. Samples were obtained on Nov. 30, 2017, 107 days after sowing for the mature state and 76 days after sowing for the flowering stage. (A) White Acatic; (B) Black Puebla; (C) Pinta; (D) Rehnborg.
Figure 4:
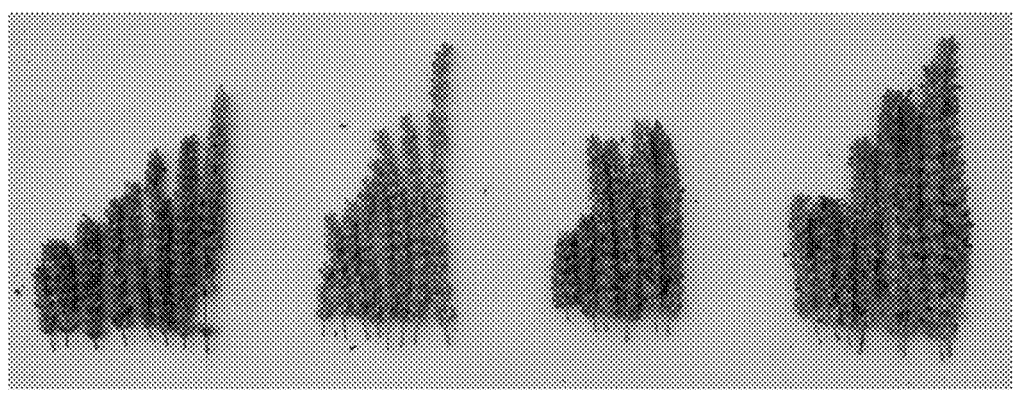
FIG. 4. Number of inflorescence per plant of four varieties of chia. The planting date was Aug. 15, 2017 and samples were obtained on Nov. 30, 2017 (107 days after sowing). (A) White Acatic; (B) Black Puebla; (C) Pinta; (D) Rehnborg.
Figure 5:
FIG. 5. Clusters per main inflorescence at physiological maturity of four varieties of chia. The planting date was Aug. 15, 2017 and samples were obtained on Nov. 30, 2017 (107 days after sowing). (A) White Acatic; (B) Black Puebla; (C) Pinta; (D) Rehnborg.
Figure 6:
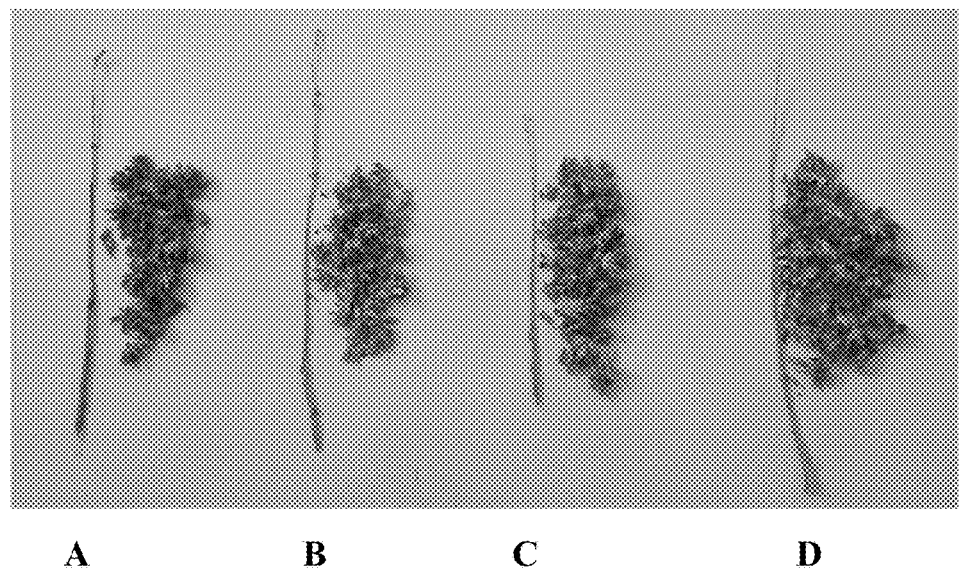
FIG. 6. Fruits per main inflorescence of four varieties of chia. The planting date was Aug. 15, 2017 and samples were obtained on Nov. 30, 2017 (107 days after sowing). (A) White Acatic; (B) Black Puebla; (C) Pinta; (D) Rehnborg.
Figure 7:
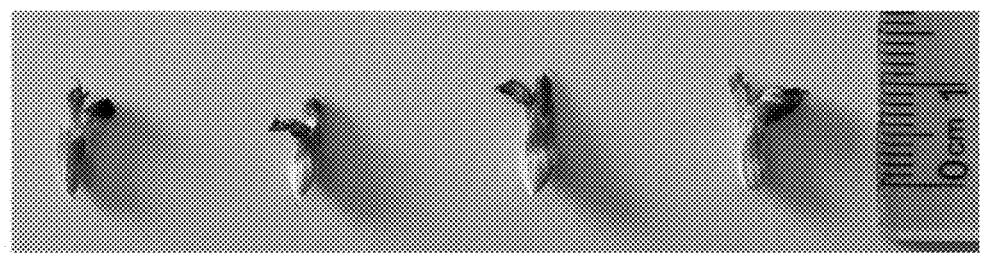
FIG. 7. Flower size of four varieties of chia. The planting date was Aug. 15, 2017 and samples were obtained on Nov. 30, 2017 (76 days after sowing). (A) White Acatic; (B) Black Puebla; (C) Pinta; (D) Rehnborg.
Figure 8:
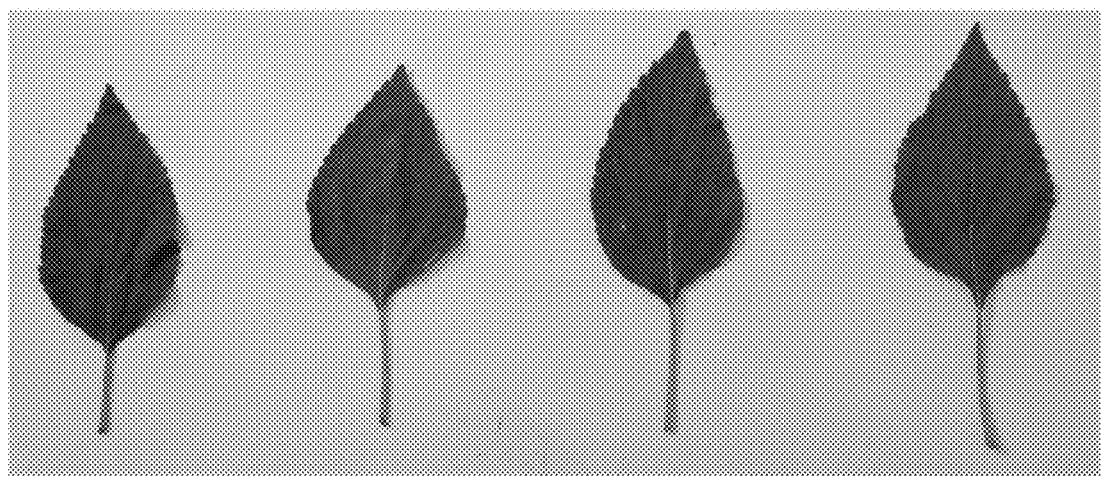
FIG. 8. Leaf shape at bottom stage of four varieties of chia. The planting date was Sep. 15, 2017 and samples were obtained on Nov. 30, 2017 (45 days after sowing). (A) White Acatic; (B) Black Puebla; (C) Pinta; (D) Rehnborg.

FIGS. 2-9 show photographic comparisons of morphological features for the four varieties of chia listed in Table 3. FIG. 2 shows the mature plant height at 107 days after sowing. FIG. 3 shows the length of the main inflorescence at the flowing stage (76 days after sowing) and physiological maturity (107 days after sowing). FIG. 4 shows the number of inflorescences per plant at physiological maturity (107 days after sowing). FIG. 5 shows the number of clusters per main inflorescence at physiological maturity (107 days after sowing). FIG. 6 shows the fruits per main inflorescence at physiological maturity (107 days after sowing). FIG. 7 shows the flower size at the flowering stage (76 days after sowing). FIG. 8 shows the leaf shape at the bottom stage (45 days after sowing). FIG. 9 shows the seed color upon harvest at 137 days after sowing.

Notable morphological and agriculturally advantageous features of the Rehnborg variety comprise: mature plant height (1760 mm), main stem length (1450 mm), stem diameter (6 mm), nodes per plant (10), inflorescences per plant (8), branches per plant (8), leaf width (68 mm), leaf length (123 mm), petiole length (60 mm), inflorescence length (250 mm), main inflorescence height about ground (1510 mm), clusters per inflorescence (30), florets per cluster (10), flower length (13 mm), calix length (7 mm), corolla length (6 mm), mass per 1000 seeds (1453 mg), and seed yield (1856 kg/ha). Without being bound by any theory, the higher seed yields of the Rehnborg variety may be due to the increased inflorescence length, increased number of clusters per inflorescence, increased flower length, increased corolla length, or a combination thereof. Other agriculturally advantageous characteristics of the Rehnborg variety are provided in the following examples.

Example 3

Increased Yield Potential

The commercial chia varieties currently available have low yield potential. It does not appear that the Heartland and Sahi Alba 914 chia varieties were selected for improved seed yields. See U.S. Pat. Nos. 8,586,831 and 9,686,926. A trial conducted in Jalisco, Mexico at three planting dates between October 2016 and May 2017 demonstrated that the Rehnborg variety had greater seed yields than the White Acatic, Pinta, and Black Puebla varieties (Table 4). Seeds were sown on Oct. 29, 2016; Dec. 15, 2016; and Jan. 20, 2017 and seed from the resulting plants was harvested on Feb. 26, 2017 (120 days after sowing); Apr. 24, 2017 (130 days after sowing); and May 25, 2017 (125 days after sowing), respectively. These results show the high productive potential of the Rehnborg variety.

TABLE 4

Agronomic performance of four varieties of chia cultivated at three sowing dates in Jalisco, Mexico during the 2016-2017 season.

| | Seed Yield (kg/ha) | | | | |
|---|---|---|---|---|---|
| Variety | Oct. 29, 2016 | Dec. 15, 2016 | Jan. 20, 2017 | Mean | Relative Yield (%) |
| Rehnborg | 2209 | 1539 | 1821 | 1856 | — |
| Pinta | 1595 | 1273 | 317 | 1062 | 75 |
| White Acatic | 1597 | 1368 | 1235 | 1400 | 33 |
| Black Puebla | 1608 | 1283 | 59 | 983 | 89 |

Relative Yield is the percent increase in the mean seed yield for the Rehnborg variety as compared to the indicated variety.

Example 4

Increased Seed Mass

A distinctive characteristic of the Rehnborg variety is its high seed mass. On average, the Rehnborg variety produces larger and heavier seeds than three other chia varieties (Table 5). Seeds were sown on Oct. 29, 2016; Dec. 15, 2016; and Jan. 20, 2017 and seed from the resulting plants was harvested on Feb. 26, 2017 (120 days after sowing); Apr. 24, 2017 (130 days after sowing); and May 25, 2017 (125 days after sowing), respectively.

TABLE 5

Mass of chia seed from four varieties of chia cultivated at three sowing dates in Jalisco, Mexico during 2016-2017.

| | Mass of One Thousand Seeds (mg) | | | | |
|---|---|---|---|---|---|
| Variety | Oct. 29, 2016 | Dec. 15, 2016 | Jan. 20, 2017 | Mean | Relative Gain (%) |
| Rehnborg | 1471 | 1456 | 1431 | 1453 | — |
| Pinta | 1291 | 1395 | 1273 | 1320 | 10 |
| White Acatic | 1239 | 1252 | 1243 | 1245 | 17 |
| Black Puebla | 1332 | 1372 | 1331 | 1344 | 8 |

Relative Gain is the percent increase in the mean mass of 1000 seeds for the Rehnborg variety as compared to the indicated variety.

Example 5

Uniformity to Flowering and Maturity

The Rehnborg variety has uniform growth timing to flowering and maturity (see Table 6). The Rehnborg variety flowers at 55 to 63 days after sowing and reaches maturity at 111 to 120 days after sowing. These characteristics permit the Rehnborg plant population to minimize damage caused by predators and reduce seed loss during harvest. White Acatic and Black Puebla have a similar performance for these two parameters; however, they have lower yields.

TABLE 6

Days to flowering and maturity for four varieties of chia cultivated in Jalisco, Mexico during 2016-2017. Planting date: Oct. 26, 2016.

| | Flowering (DAS) | | | Maturity (DAS) | | |
|---|---|---|---|---|---|---|
| Variety | Begin | End | Period | Begin | End | Period |
| Rehnborg | 55 | 63 | 8 | 111 | 120 | 9 |
| Pinta | 54 | 70 | 16 | 107 | 122 | 15 |
| White Acatic | 55 | 65 | 10 | 110 | 118 | 8 |
| Black Puebla | 58 | 68 | 10 | 115 | 123 | 8 |

DAS: Days after sowing

Example 6

Improved Seed Production During the Winter-Spring Season

The typical varieties of chia currently cultivated in Mexico are not able to produce significant seed yields when they are planted and grown in the Winter-Spring season (see Table 7). The Rehnborg variety has higher seed yields during the winter season. The White Acatic variety is capable of producing seed during the winter season; however, it has lower yields than the Rehnborg variety. In addition, as shown in FIG. 11, the Black Puebla and Pinta varieties were incapable of reaching physiological maturity when planted during the winter season.

TABLE 7

Agronomic performance of four varieties of chia cultivated during 2017 in Jalisco, Mexico. Planting date: Jan. 20, 2017; harvested on May 15, 2017 (114 days after sowing)

| | | Plants (percent reaching stage) | | |
|---|---|---|---|---|
| Variety | Seed Yield (kg/ha) | Maturity | Flowering | Vegetative |
| Rehnborg | 1821 | 100 | 0 | 0 |
| Pinta | 317 | 50 | 50 | 0 |
| White Acatic | 1235 | 100 | 0 | 0 |
| Black Puebla | 59 | 10 | 60 | 30 |

Example 7

Improved Fertilizer Response

The high genetic uniformity of the Rehnborg variety allows it to be more efficient in utilizing applied nitrogen fertilizer to produce seed. The high yield potential of this cultivar is correlated with the high response to fertilizer, especially nitrogen-rich fertilizers. On average, the Rehnborg variety produces 11.2 kg of seed per kg of nitrogen applied. This value is greater than the nitrogen use efficiency observed for the other three Mexican cultivars typically grown (see Table 8). The nitrogen use efficiency values for the Rehnborg, White Acatic, Black Puebla, and Pinta were 11.2, 7.0, 6.6, and 5.5 kg of seed per kg of N applied, respectively.

TABLE 8

Response to nitrogen of four varieties of chia cultivated at Jalisco, Mexico. Planting date: Oct. 27, 2016; harvest date: Feb. 24, 2017 (120 days after sowing).

| | Seed Yield (kg/ha) Nitrogen Rate (kg N/ha) | | Yield Gain for | Nitrogen Use Efficiency |
|---|---|---|---|---|
| Variety | $N_0$ | $N_{100}$ | N Applied | (kg seed/kg N) |
| Rehnborg | 1090 | 2209 | 1119 | 11.2 |
| Pinta | 1045 | 1595 | 550 | 5.5 |
| White Acatic | 897 | 1597 | 700 | 7.0 |
| Black Puebla | 947 | 1608 | 661 | 6.6 |

Nitrogen Use Efficiency: (Seed Yield at $N_{100}$ − Seed Yield at $N_0$)/100 kg N Because of the high genetic uniformity that the Rehnborg variety presents, in the future, it could be used as first (male parent) or second parent (female parent) to generate hybrids. The hybrid plants usually have higher seed yields than varieties generated through selection. In addition, this cultivar could be used to transfer the uniform color, increased seed mass, and increased yield traits to other cultivars through traditional breeding or transgenic methods.

Example 8

Seed Yields in the Fall-Winter Season

The best seed yields with the Rehnborg variety are achieved when it is sown during the fall and winter seasons. An advantage for planting in the fall and winter is that it is not necessary to apply pesticides or comparable organic products to control insects and diseases. It is advantageous to apply a balanced fertilizer comprising 200, 100, 200, 250, and 50 kg/ha of N, $P_2O_5$, $K_2O$, S, respectively, and a mixture of micronutrients in order to achieve high seed yields (Table 9).

TABLE 9

Rehnborg variety flowering, maturity, and seed yields as a function of planting date in Jalisco, Mexico during the 2016-2017 fall-winter season.

| Planting Date | Flowering (DAS) | Physiol. Maturity (DAS) | Seed Yield (kg/ha) |
|---|---|---|---|
| Oct. 15, 2016 | 58 | 105 | 1926 |
| Nov. 15, 2016 | 64 | 112 | 2544 |
| Dec. 15, 2016 | 68 | 115 | 2909 |
| Jan. 15, 2017 | 68 | 115 | 1431 |

DAS: days after sowing

Example 9

Seed Yields in the Summer Season

The Rehnborg variety can also be planted during the summer season. Pesticides or comparable organic products are typically required during the summer season to control insects and diseases. The seed yield is typically lower in the summer season compared with that obtained in the fall and winter seasons (Table 10; cf Table 9).

TABLE 10

Rehnborg variety maturity and seed yields as a function of summer planting date and pesticide application in Jalisco, Mexico during 2016-2017.

| Planting date | Pesticide Application(s) | Physiological Maturity (DAS) | Seed Yield (kg/ha) |
|---|---|---|---|
| Jul. 15, 2016 | None | 135 | 810 |
| Jul. 15, 2016 | Three | 135 | 1122 |
| Aug. 15, 2016 | None | 151 | 1126 |
| Aug. 15, 2016 | Three | 150 | 1867 |
| Sep. 15, 2016 | None | 139 | 1796 |
| Sep. 15, 2016 | Three | 140 | 1858 |

DAS: days after sowing

Biological Deposits

A representative sample of seeds of chia (*Salvia hispanica* L.) variety Rehnborg was deposited with the American Type Culture Collection (ATCC), 10801 University Blvd., Manassas, Va., 20110, United States of America on Feb. 13, 2018 and was assigned ATCC Patent Deposit Designation PTA-124758 on Mar. 13, 2018. The deposit will be maintained at the ATCC depository under the terms of the Budapest Treaty on the International Recognition of the Deposit of Microorganisms for the Purposes of Patent Procedure for a term of at least thirty years and at least five years after the most recent request for the furnishing of a sample of the deposit was received by the depository. Applicants have satisfied all the requirements of 37 C.F.R. §§ 1.801-1.809, including providing an indication of the viability of the sample. Additional deposits will be made at the ATCC as needed to ensure availability, subject to the conditions described herein. Applicants impose no restrictions on the availability of the deposited material from the ATCC after the issuance of a patent from this application. Applicants have no authority to wave any restrictions imposed by law on the transfer of biological material or its transportation in worldwide commerce. Applicants do not waive any of their rights granted under any patents issuing from this application in any country or under the U.S. Plant Variety Protection Act (7 U.S.C. § 2321 et seq.) or other international or foreign plant variety protection systems.

What is claimed is:

1. A seed of chia (*Salvia hispanica* L.) variety designated Rehnborg, a representative sample of seed having been deposited under ATCC Patent Deposit Designation PTA-124758.

2. The seed of claim 1, wherein the seed has a uniform white color.

3. The seed of claim 1, wherein the seed has an average seed mass of at least about 1400 mg/1000 seeds.

4. A plant product produced from one or more of the seeds of claim 1, wherein the plant product comprises a cell of the chia seed.

5. The plant product of claim 4, wherein the product comprises chia seed, oil, meal, protein, fiber, derivatives thereof, or combinations thereof, wherein the plant product comprises a cell of the chia seed.

6. Chia oil or meal produced from one or more of the seeds of claim 1, wherein oil or meal comprises a cell of the chia seed.

7. A cosmetic or beauty product comprising chia oil produced from one or more of the seeds of claim 1, wherein the oil comprises a cell of the chia seed.

8. A food product comprising the chia seed of claim 1, wherein the food product comprises a cell of the chia seed.

9. A chia plant, or part thereof, produced by growing the seed of claim 1.

10. A homogenous population comprising a plurality of the chia plant of claim 9.

11. The homogenous population of claim 10, wherein the population yields an average of at least about 1500 kilograms of seed per hectare.

12. The chia plant of claim 9, wherein the chia plant comprises or confers to its seed one or more traits comprising increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants or wild type chia.

13. A tissue culture of cells produced from the chia plant of claim 9, wherein the cells are produced from a plant part comprising embryo, meristematic cell, leaf, cotyledon, hypocotyl, root, root tip, stem, pistil, anther, ovule, flower, pollen, or seed.

14. A chia (*Salvia hispanica* L.) plant regenerated from the tissue culture of claim 13, wherein the chia plant comprises the morphological and physiological characteristics of variety Rehnborg, a representative sample of seed having been deposited under ATCC Patent Deposit Designation PTA-124758.

15. A chia (*Salvia hispanica* L.) plant or plant part of the variety designated Rehnborg, a representative sample of seed having been deposited under ATCC Patent Deposit Designation PTA-124758.

16. A homogenous population comprising a plurality of the chia plant of claim 15, wherein the population yields an average of at least about 1500 kilograms of seed per hectare.

17. Seed produced from the plant of claim 15.

18. The seed of claim 17, wherein the seed has a uniform white color.

19. The seed of claim 17, wherein the seed has an average seed mass of at least about 1400 mg/1000 seeds.

20. The plant of claim 15, wherein the plant or plant part comprises one or more traits comprising increased seed color uniformity, increased seed yield, increased seed mass, increased oil yield, increased protein yield, increased fiber yield, increased fertilizer utilization, improved adaptation to winter planting, increased drought tolerance, increased cold tolerance, increased photoperiod, herbicide tolerance, increased insect resistance, increased disease resistance, or combinations thereof, as compared to other varieties of chia plants or wild-type chia.

21. A chia plant, or part thereof, produced by growing the seed of the plant of claim 15, wherein the plant, or part comprises one or more traits comprising uniform white seed color, increased seed yield, increased seed mass, increased oil yield, increased protein yield, increased fiber yield, increased fertilizer utilization as compared to other varieties of chia plants or wild-type chia.

22. A germplasm of chia (*Salvia hispanica* L.) variety designated Rehnborg, a representative sample of seed having been deposited under ATCC Patent Deposit Designation PTA-124758.

23. A chia plant comprising the chia germplasm of claim 22.

24. Seed produced by the chia plant of claim 23, a representative sample of seed having been deposited under ATCC Patent Deposit Designation PTA-124758.

25. The seed of claim 24, wherein the seed has a uniform white color.

26. The seed of claim 24, wherein the seed has an average seed mass greater than about 1400 mg/1000 seeds.

27. A homogenous population of chia plants of claim 23, wherein the population yields an average of at least about 1500 kilograms of seed per hectare.

\* \* \* \* \*